United States Patent [19]

Goodman

[11] Patent Number: 4,763,524
[45] Date of Patent: * Aug. 16, 1988

[54] AUTOMATIC UNDERWATER ACOUSTIC APPARATUS

[75] Inventor: Jerome Goodman, Baltimore, Md.

[73] Assignee: The United States of America as represented by the Secretary of the Navy, Bethesda, Md.

[*] Notice: The portion of the term of this patent subsequent to Mar. 10, 2004 has been disclaimed.

[21] Appl. No.: 943,413

[22] Filed: Dec. 19, 1986

Related U.S. Application Data

[63] Continuation-in-part of Ser. No. 728,889, Apr. 30, 1985, Pat. No. 4,648,275.

[51] Int. Cl.$^4$ .................................. G01N 29/00
[52] U.S. Cl. ............................................. 73/589
[58] Field of Search ................. 73/589, 599; 310/337, 310/358

[56] References Cited

U.S. PATENT DOCUMENTS

| | | | |
|---|---|---|---|
| 2,645,933 | 7/1953 | Arenberg | 73/67 |
| 2,768,524 | 10/1986 | Beard | 73/53 |
| 4,184,093 | 1/1980 | Sullivan | 310/337 |
| 4,268,912 | 5/1981 | Congdon | 310/337 |
| 4,412,148 | 10/1983 | Klicker et al. | 310/358 |
| 4,422,003 | 12/1983 | Safari et al. | 310/358 |
| 4,542,644 | 9/1985 | Claytor et al. | 73/61 R |
| 4,638,468 | 1/1987 | Francis | 310/318 |
| 4,648,275 | 3/1987 | Goodman | 73/589 |
| 4,656,384 | 4/1987 | Magoni | 310/340 |
| 4,668,964 | 5/1987 | Padalino et al. | 310/340 |
| 4,683,396 | 7/1987 | Takeuchi et al. | 310/358 |

FOREIGN PATENT DOCUMENTS

| | | | |
|---|---|---|---|
| 2020024 | 11/1979 | United Kingdom | 73/589 |
| 0480973 | 12/1975 | U.S.S.R. | 73/589 |

OTHER PUBLICATIONS

EugenSkudrzyk, Die Grundlagen Der Akustik, Springer Verlag, Wien, 1954, p. 772.

Primary Examiner—Stewart J. Levy
Assistant Examiner—Lawrence G. Fess
Attorney, Agent, or Firm—Luther A. Marsh; Thomas S. O'Dwyer

[57] ABSTRACT

An automatic underwater acoustic impedance measuring apparatus is instrumented with transducers whose outputs are led to a computer for the automatic measurement of acoustic impedance. One hydrophone is positioned so that it senses the incident and reflected signals to compute reflection factor. A second hydrophone is positioned at the face of the sample so that is senses the incident and reflected waves from which it is possible to compute the phase angle. Acoustic impedance is obtained from the phase angle and reflection factor, computed and printed out in real time and automatically swept through a frequency range of interest.

3 Claims, 1 Drawing Sheet

FLEXIBLE CERAMIC

AUTOMATIC UNDERWATER ACOUSTIC APPARATUS

The invention described herein may be manufactured and used by or for the Government of the United States of America for governmental purposes without the payment of any royalties thereon or therefor.

CROSS-REFERENCES TO RELATED APPLICATIONS

This application is a continuation in part of application Ser. No. 06/728,899 filed Apr. 30, 1985 now U.S. Pat. No. 4,648,275 issued on Mar. 10, 1987.

BACKGROUND OF THE INVENTION

1. Field of the Invention

This invention is directed to an automatic underwater acoustic apparatus for measuring impedance.

2. Description of the Prior Art

A pulse tube has traditionally been used as the apparatus for impedance measurement commencing with the efforts of Erwin Meyer and Eugen Skudryzk, German professors, to develop underwater acoustic absorbers for the German Navy during World War II. Physically, the pulse tube is a thick walled steel structure filled with water and instrumented with acoustic transducers. A gated sine wave with about five cycles to approximate a plane wave is the acoustic signal that is employed. Some tubes are equipped to provide temperature and hydrostatic pressure control for studying samples subjected to varying environmental stimuli.

Typical dimensions of various pulse tubes are as follows:

| Length (feet) | 7 | 42 | 21 | 42 |
|---|---|---|---|---|
| Inner Diameter (inches) | 2 | 5.56 | 2.50 | 3.40 |
| Wall Thickness (inches) | 1 | 2.22 | 2.75 | 2.30 |

An acoustic signal is generated at the bottom of the tube to be reflected from the sample, mounted at the top, which is attached to a high impedance backing, or mounted against a layer of gas acting as a low impedance backing or mounted in the center so that there is a water backing. A portion of the signal is reflected and its phase is shifted by the sample. The percentage of energy reflected is expressed as the reflection coefficient. Acoustic impedance can be obtained from a knowledge of the reflection coefficient and of the phase shift.

The conventional method of measuring impedance in a water filled impedance tube processes the reflected signal by nulling it with a known signal of equal amplitude and opposite phase. This is conventionally manually performed by an operator at discrete frequencies and represents a long and tedious process subject to error and to operator fatigue.

One recent example, U.S. Pat. No. 4,305,295 illustrates a portable apparatus for measuring acoustic impedance in air at the surface of curved sound absorber wherein the apparatus consists of a circular, flexible disc held at a constant distance from a curved absorbing surface by pins or flexible ribs. Sound from a loudspeaker is fed to the center of the discs and allowed to propagate radially in the space between the disc and absorber. Radial arrays of microphones on the disc surface sense sound pressure amplitude and phase, from which impedance is calculated. Such apparatus is used for determining the acoustic properties of absorbing linings as installed in ducts of jet engines. It is also applicable for measuring the acoustic impedance of other absorptive surfaces, including for example, acoustic wall and ceiling panels. Another example is illustrated in U.S. Pat. No. 4,289,143 wherein there is described a method of and apparatus for audiometrically determining the acoustic impedance of a human ear in air.

The measuring of underwater acoustic impedance of various materials and acoustic structures is required in the use of such materials and structures such as absorbers, decouplers, sonar domes, and transducers. The acoustic impedance of a material or of an acoustic structure provides significant information regarding the operating parameters or attributes of the structure or of its components. The interpretation and examination of an impedance locus reveals the magnitude of acoustic absorption, reflection, sonic velocity, elastic moduli, dissipation and resonance frequencies. These qualities are measured for purposes related to material development, for evaluation, for product development and for quality control. Some of the hydroacoustic applications derived from acoustic impedance information are manifested as underwater absorbers, reflectors, transducers, sonar domes, and baffles. Dynamic moduli, useful in non-acoustic and in air acoustic applications, are also determined from acoustic impedance information obtained with the use of an underwater acoustic impedance measuring apparatus.

SUMMARY OF THE INVENTION

The present invention provides an automatic underwater acoustic impedance measuring apparatus comprising transducer means properly located on said apparatus to produce an acoustic signal, one transducer means positioned so that it senses the incident signals and reflected signals to compute reflection factor, a third transducer means positioned at the face of sample material so that it senses the incident and reflected waves to compute the phase angle, said transducer means properly interfaced with a computer means for automatically computing and a printing means for printing out in real time the acoustic impedance.

OBJECTS OF THE INVENTION

An object of the invention is to provide an automatic underwater acoustic impedance measuring apparatus.

Another object of the invention is to provide an automatic underwater acoustic impedance measuring apparatus with enhanced performance.

Still another object of the invention is to provide an automatic underwater acoustic impedance measuring apparatus which automatically computes and prints out a frequency range of interest.

Other objects and many of the attendant advantages and usage of the invention will be readily observed and appreciated as the same becomes better understood by reference to the following detailed description.

DESCRIPTION OF THE PREFERRED EMBODIMENT

Figure 1:
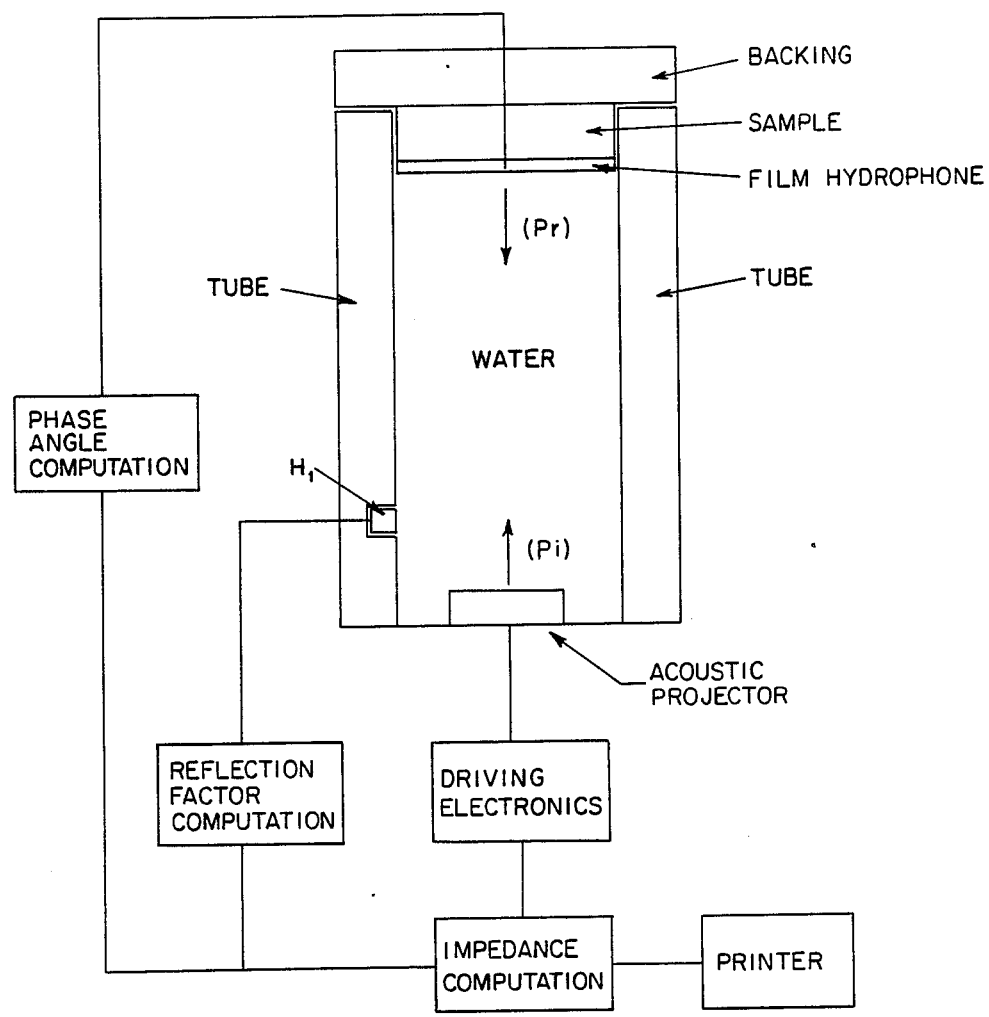
FIG. 1 is a cross-sectional view of the automatic underwater acoustic apparatus of the invention.
Figure 2:
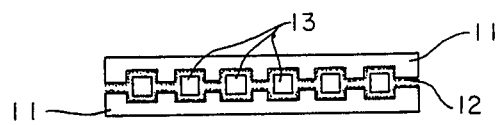
FIG. 2 illustrates the use of a flexible ceramic material as an alternative to the film hydrophone.

The drawing shows an embodiment of the automatic underwater acoustic impedance measuring apparatus of the invention. A projector, a hydrophone that is flush mounted in the tube wall and a film hydrophone on the face of the sample are the sensors. A sample material is mounted so that its face is covered with a thin film hydrophone or hydrophone of very small thickness and acoustic transparency. Its electrical output can be led out through the backing located at the top of the tube.

The film polymer hydrophones are fabricated from sheets of polyvinylidene fluoride (PVDF). Piezoelectric properties are imparted to the material by allowing cooling to ambient room temperature while subjected to an intense electrostatic field. The process is similar to the manufacture of film electrets which are the electric analog of a permanent magnet. Manufacturers of the material include Thorn-EMI of Great Britain and the Pennwalt Corporation of Chester, Pa. Acoustic transparency is an attribute of the thin film polymer hydrophone that is employed advantageously herein as the hydrophone does not alter the acoustic properties of the sample to which it is attached. The thin film polymer preferred is about 0.0025 inch in thickness and is flat. The electrical output of the hydrophone is fed through leads that pierce the sample and that are led to the computer processing the phase angle data.

The "flexible ceramic" is made from two thin sheets of an encapsulate polymeric film 11, such as, polyurethane or polybutadiene onto which is sprayed a thin film silver surface 12 which acts as electrodes, said electrodes are positioned so as to face each other, then thin strips of a piezoceramic material 13, such as, lead zirconate titanate are placed between the electroded surfaces. The piezoceramic is not flexible; however, the configuration is flexible and it can assume the shape of a curved surface.

The electrical signal produced by a gated sine wave at the hydrophone located at the sample face, is the sum of the incident ($P_i$) and reflected signals ($P_r$). Incident pressure is "$P_i$". The reflected signal ($P_r$) is modified by the reflection factor "R" of the sample material and by its associated phase angle "$\theta$". Reflection factor $$R = \left(\frac{Pr}{Pi}\right)^2$$

is measured by $H_1$. Through algebraic manipulation the magnitude of the film hydrophone voltage is determined by the following formula:

$$Pi(1+2R\cos\theta+R^2)^{\frac{1}{2}}$$

The reflection factor is obtained from the output of the flush mounted hydrophone $H_1$ by obtaining the ratio of the reflected to the incident signals. Consequently, it is possible to determine the phase angle from the output of the hydrophone mounted on the sample and thus the acoustic impedance of the sample.

An integral part of the apparatus is a dedicated computer. First, a frequency range of interest is selected, e.g. 2k Hz to 9k Hz, with fine increments such as 100 Hz and the dedicated computer is programmed to sweep the selected range automatically. Second, the reflection factor (R) is obtained from hydrophone $H_1$ and it is applied to the output of the sample mounted hydrophone which computes the phase angle $\theta$. Third, the values of "R" and "$\theta$" are fed into a program for automatically calculating, printing and plotting acoustic impedance.

Obviously, many modifications and variations of the present invention are possible in light of the above teachings. It is therefore to be understood that within the scope of the appended claims, the invention may be practiced otherwise than as specifically described.

What is claimed is:

1. An automated underwater acoustic impedance measuring apparatus comprising:
   (a) a first transducer means positioned within said apparatus for producing and transmitting a plane wave,
   (b) a second transducer means positioned within said apparatus for sensing incident signals and reflected signals of a sample material placed within the apparatus for reflection factor computation,
   (c) a third transducer means positioned within said apparatus on the face of the sample material selected from the group consisting of a thin flat film polymer and a flat flexible ceramic means for sensing combined incident waves and reflected waves for phase angle computation,
   (d) computer means positioned and interfaced with said second transducer means and said third transducer means for automatically computing real time acoustic impedance in accordance with formula:

$$R = \left(\frac{Pr}{Pi}\right)^2,$$

and $$Pi(1+2R\cos\theta+R^2)^{\frac{1}{2}}$$

wherein:
R = reflection factor
Pr = reflected sound pressure
Pi = incident sound pressure
$\theta$ = phase angle of the acoustic impedance
obtained from the reflection factor derived from the second transducer means and obtained from the phase angle derived from the third transducer means, and
   (e) indicating means for indicating said acoustic impedance.

2. An automated underwater acoustic impedance measuring apparatus as in claim 1 wherein the third transducer means is a thin flat film polymer means.

3. An automated underwater acoustic impedance measuring apparatus as in claim 1 wherein the third transducer means is a flat "flexible ceramic" means.

* * * * *